United States Patent [19]

El-Sayad et al.

[11] Patent Number: 4,701,460

[45] Date of Patent: Oct. 20, 1987

[54] LONG DURATION NEUROMUSCULAR BLOCKING AGENTS

[75] Inventors: Hassan A. El-Sayad, Chapel Hill; Roy A. Swaringen, Jr., Durham; David A. Yeowell, Chapel Hill, all of N.C.

[73] Assignee: Burroughs Wellcome Co., Research Triangle Park, N.C.

[21] Appl. No.: 694,908

[22] Filed: Jan. 25, 1985

Related U.S. Application Data

[63] Continuation of Ser. No. 217,444, Dec. 17, 1980, abandoned.

[51] Int. Cl.$^4$ .................. A61K 31/47; C07D 401/12
[52] U.S. Cl. .................................. 514/308; 546/140
[58] Field of Search ..................... 546/140; 514/308

[56] References Cited

U.S. PATENT DOCUMENTS

| | | | |
|---|---|---|---|
| 3,004,031 | 10/1961 | Taylor et al. | 546/140 |
| 4,179,507 | 12/1979 | Stenlake et al. | 546/140 |
| 4,192,877 | 3/1980 | Savarese et al. | 546/140 |
| 4,491,665 | 1/1985 | El-Sayad et al. | 546/140 |

FOREIGN PATENT DOCUMENTS

| | | |
|---|---|---|
| 863717 | 3/1961 | United Kingdom . |
| 1579822 | 11/1980 | United Kingdom . |

OTHER PUBLICATIONS

Nature, Nov. 22, 1958, vol. 182, pp. 1424–1426.
Journal of the Chemical Society, Gladych and Taylor, 1481–1487, (1962), p. 1483.

Primary Examiner—Glennon H. Hollrah
Assistant Examiner—James H. Turnipseed
Attorney, Agent, or Firm—Donald Brown

[57] ABSTRACT

Long duration muscle relaxant compound of formula (I)

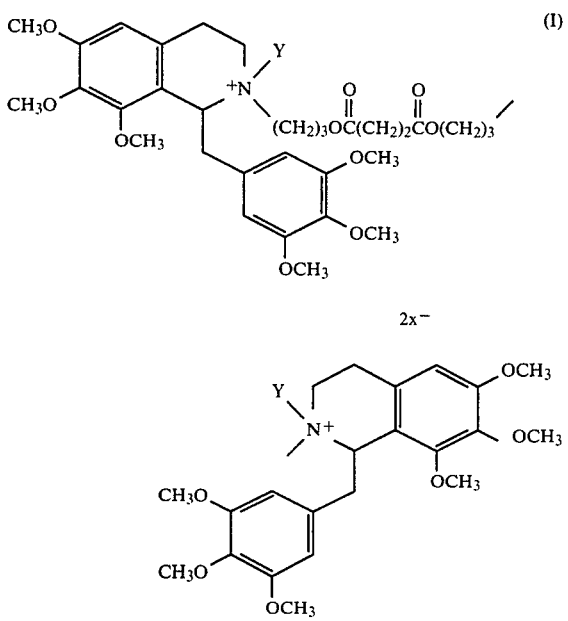

and its use in producing muscle relaxation in mammals including man.

12 Claims, No Drawings

LONG DURATION NEUROMUSCULAR BLOCKING AGENTS

This application is a continuation of application Ser. No. 217,444 filed Dec. 17, 1980, now abandoned.

Background of the Disclosure

In anesthesia, neuromuscular blocking agents are used to provide skeletal muscle relaxation during surgery and during intubation of the trachea.

In general there are two types of neuromuscular blocking agents in use, non-depolarizing and depolarizing.

The non-depolarizing agents include d-tubocurarine, pancuronium, gallamine, diallyltoxiferine and toxiferine.

The depolarizing agents include succinylcholine and decamethonium. All of the conventional non-depolarizing agents when used for producing skeletal muscle relaxation in surgery have a long duration of action, e.g. 60 to 180 minutes in man. The conventional depolarizing agents, on the other hand, provide muscle relaxation with duration of action shorter than that of the non-depolarizing agents.

For example, succinylcholine provides a short duration of action of about 5 to 15 minutes whereas decamethonium provides about 20 to 40 minutes duration of muscle relaxation in man.

Each non-depolarizing agent has inherent side effects. For example, gallamine and pancuronium may cause tachycardia, and d-tubocurarine and diallyltoxiferine may cause hypotension.

While these drugs can be pharmacologically antagonized with anticholinesterase agents, this obviously necessitates the administration of a second drug which itself may have its own side effects, e.g., bradycardia, gut spasm and bronchorrhea. Thus, to overcome the aforementioned side effects of the anticholinesterase agents, a third drug, an anticholinergic drug, e.g. atropine must also be given.

Surprisingly, the compounds of the present invention have a very high potency, long duration of action and are free of any side effects at the dosages anticipated being used clinically. Furthermore, the trans compound where Y is methyl has shown unexpectedly superior activity (potency) and surprisingly much longer duration than any of their analogs, i.e., compounds with different chain lengths and the same isoquinoline base or compounds with different bases and the same chain length.

Accordingly, this invention provides new neuromuscular blocking agents (sometimes called muscle relaxants) of the formula (I):

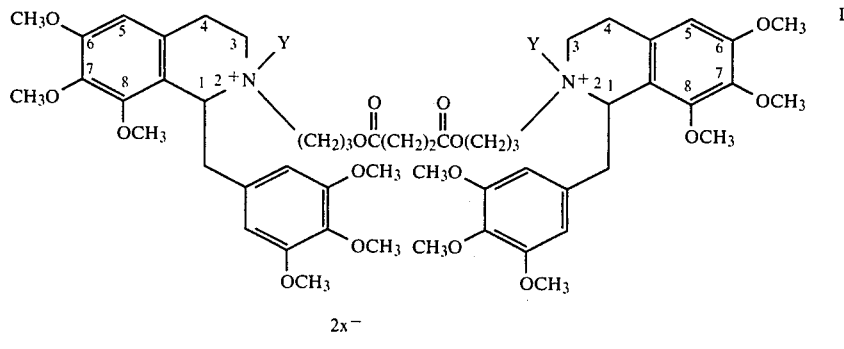

wherein Y is lower alkyl of 1–4 carbon atoms (methyl, ethyl, propyl or butyl); $X^-$ is an anion, preferably pharmaceutically acceptable and preferably the trimethoxybenzyl group at the 1 position and the $(CH_2)_3$ (also known as substituted propyl) of the group $(CH_2)_3OCO(CH_2)_2OCO(CH_2)_3$ at the 2 position are in a trans relationship relative to each other in the nitrogen-containing ring.

The preferred compound is that wherein Y is methyl.

Since the activity of the compounds of the invention resides in the di-cation, the nature of the anion $X^-$ is relatively unimportant. Suitable pharmaceutically acceptable anions include iodide, mesylate, tosylate, bromide, chloride, sulphate, phosphate, hydrogen phosphate, acetate, benzenesulphonate, succinate, maleate, naphthalenesulphonate and propionate.

The compounds of the invention are preferably prepared as an approximately 1:1 mixture of the racemic (dl) pair and the meso-isomer. This invention further provides means for obtaining the compounds of formula (I) when in the form of one of the aforesaid isomers substantially free of the other isomers, and mixtures of one of the isomers with one or both of the other isomers. Other methods of preparing the cis-trans mixtures are well known in the art.

It is preferred that the compounds of the invention be provided in a form where the ratio of the trans, trans compound of the invention to the total of any corresponding cis, cis and cis, trans compounds present as impurities is at least 96:4.

The compounds of formula (I) are used as neuromuscular blocking agents in conjunction with surgery or for intubation of the trachea by conventional parenteral administration, e.g. intra-muscular or intravenous administration in solution. The compounds of the present invention shown in formula (I) are administered to subjects such as monkeys and man (humans) and other mammals to achieve a neuromuscular block. The dosage for each type of subject will vary because of the peculiarities of the species. However, a suitable intravenous amount or dosage of the compounds of formula (I) to obtain paralysis in mammals would be 0.004 to 0.03 mg/kg of body weight, and most preferably 0.01 to 0.02 mg/kg of body weight, the above being based on the weight of the di-cation which is the active ingredient. The compounds of this invention are, therefore, clearly more potent than the agents most widely used clinically (pancuronium 0.06–0.08 mg/kg, d-tubocurarine 0.4–0.6 mg/kg). The dosage for intramuscular administration is two to four times the intravenous dose. The compounds of this invention are reversible using conventional anticholinesterase agents such as neostigmine and edrophonium and appear to avoid the side effects associated with the non-depolarizing agents.

The compounds of formula (I) are therefore useful for producing a long duration neuromuscular blockade in man as well as in other mammals, and the present invention provides a method of producing such blockade in mammals by intravenously injecting a dose of 0.004 to 0.03 mg/kg to the mammal. It should be understood that the duration in a mammal such as monkey is considerably shorter than in humans and is considered a long duration agent for that species.

The compounds may be presented in a pharmaceutical formulation for parenteral administration. The formulation may be an aqueous or non-aqueous solution or emulsion in a pharmaceutically acceptable liquid or mixture of liquids, which may contain bacteriostatic agents, antioxidants, buffers, thickening agents, suspending agents or other pharmaceutically acceptable additives. Such formulations are normally presented in unit dosage forms such as ampoules or disposable injection devices, or in multidose forms such as a bottle from which the appropriate dose may be withdrawn, all such formulations should be sterile.

The compounds of this invention may be presented as a powder, e.g. as a unit dose in a sealed vial to which sterile water or other pharmaceutically acceptable sterile liquid vehicle may be added, preferably by aseptic techniques.

A suitable unit dose to obtain a neuromuscular block for adult humans (~150 lb) is about 0.15 mg to 2.5 mg and most preferably 0.5 to 1.5 mg.

The compounds of this invention if desired may be administered in conjunction with depolarizing agents such as listed above.

Thus a suitable pharmaceutical parenteral preparation for administration to humans will preferably contain 0.3 to 2.5 mg of the compounds of formula (I) of this invention in solution.

A simple and preferred formulation is a solution of the compound of formula (I) in water which may be prepared by simply dissolving the compound into previously sterilized pure water, i.e. pyrogen free water under aseptic conditions and sterilizing the solution.

The compound of formula (I) may also be administered as an infusion of a dextrose solution or a saline solution, e.g. Ringers' solution.

The compounds may also be administered in other solvents such as alcohol, polyethylene glycol and dimethylsulphoxide. They may also be administered intramuscularly as a suspension.

The compounds of formula (I) may be prepared by the coupling of a trans-N-alkyl-N-3-hydroxypropyl-1,2,3,4-tetrahydro6,7,8-trimethoxy-2-(3,4,5-trimethoxybenzyl)isoquinolinium salt with succinic acid or a reactive derivative thereof such as succinic anhydride or succinyl chloride.

EXAMPLE 1

5',8-Dimethoxylaudanosine (27.2 g) and iodopropanol (27.2 g) were refluxed in 150 mL of dry acetone for 21 hrs. The solvent was evaporated under vacuum and the unreacted iodopropanol was extracted with 100 mL of diethyl ether. The ether was decanted and the residue was dissolved in 300 mL at hot ethyl alcohol and cooled at 5° for 16 hrs to yield 29.2 g of a 9/1 mixture at the trans/cis quaternary iodides as indicated by High Performance Liquid Chromatography (HPLC). The mixture was recrystallized twice from ethyl alcohol to give 24.4 g of trans-N-3-hydroxypropyl-5', 8-dimethoxylaudanosinium iodide (98% trans by HPLC). The iodide salt was converted to the chloride salt by passing its methanolic solution through a column packed with 75 g of Dowex 1-X8 ion exchange resin. The solvent was evaporated under vacuum and 100 mL of acetone was added to give 18.1 g of trans-N-3-hydroxypropyl-5',8dimethoxylaudanosinium chloride (100% trans by HPLC). The yield was 67% overall.

Calculated for $C_{26}H_{38}NO_7Cl_2.2H_2O$: C, 56.98; H, 7.72; N, 2.56; Cl, 6.47. Found: C, 56.97; H, 7.74; N, 2.52; Cl, 6.47.

EXAMPLE 2

Trans-N-3-hydroxypropyl-5',8-dimethoxylaudanosinium chloride (>99% trans by HPLC, 2 g) was suspended in 150 mL of 1,2-dichloroethane at 70° and succinyl chloride (0.24 g) was added. The mixture was heated at reflux for 140 minutes. The solvent was removed under vacuum to give an amorphous solid which was dissolved in 100 mL of chloroform and washed with 5% aqueous sodium chloride solution 8×100 mL to remove the unreacted quaternary salt. The chloroform layer was washed with 50 mL of water, dried and evaporated under vacuum. The residual amorphous solid was dissolved in water and lyophilized to give 0.5 g of trans. trans-2,2'-(Dimethylenebis(carbonyloxytrimethylene))bis(1,2,3,4 tetrahydro-6,7,8-trimethoxy-2-methyl-1-(3,4,5-trimethoxybenzyl)isoquinolinium) dichloride which was assayed by High Performance Liquid Chromatography (HPLC) as 100%.

Calculated for $C_{56}H_{78}N_2O_{16}$ 2 Cl 6 $H_2O$: C, 55.39; H, 7.47; N, 2.31; Cl, 5.83. Found: C, 55.72; H, 7.04; N, 2.27; Cl, 5.84.

EXAMPLE 3

Mescaline and 3,4,5-trimethoxyphenylacetic acid were reacted in xylene to give the corresponding amide which was cyclized to the corresponding dihydroisoquinoline via the Bischler-Napieralski reaction followed by reduction and reductive methylation to give 5', 8-dimethoxylaudanosine mp 174–176.

EXAMPLE 4 trans, trans-2,2'-(Dimethylenebis(carbonyloxytrimethylene))- . bis(1,2,3,4-tetrahydro-6,7,8-trimethoxy-2-methyl-1-(3,4,5-trimethoxybenzyl)isoquinolinium) dichloride was examined by intravenous administration to cats and Rhesus monkies, maintained by artificial ventilation and prepared for recording the isometric twitch of the tibialis anterior muscle in response to stimulation of peroneal nerve. The results are shown in the following table.

| | Cat | | | Rhesus Monkey | |
|---|---|---|---|---|---|
| # of Animals | $ED_{95}$ mg/kg | *Duration Minute | # of Animals | $ED_{95}$ mg/kg | *Duration Minute |
| 2 | 0.01 | ~60 | 2 | 0.015 | ~30+ |

*The time from injection to 95% recovery
+This translates to about 90 minutes in man.

We claim:
1. A compound of the formula

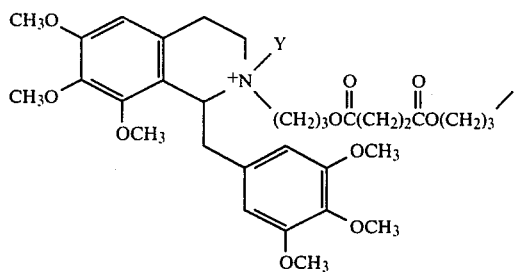

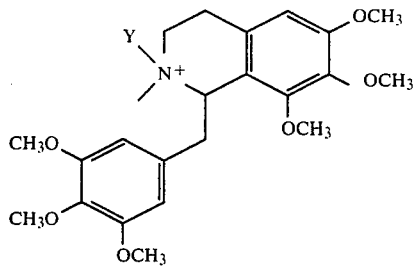

2x⁻

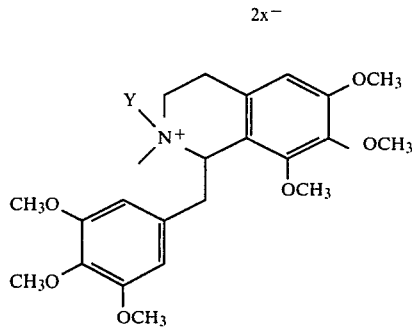

wherein X is a pharmaceutically acceptable anion.

2. A mixture comprising the mixture of the racemic (dl) pair ad the meso-isomer of the compound of the formula

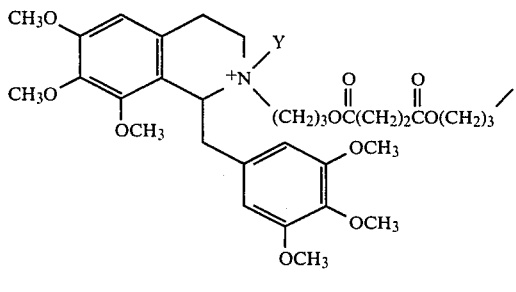

2x⁻

3. A pharmaceutically acceptable salt comprising the cation trans-; trans-2,2,'-(dimethylenebis;(carbonyloxytrimethylene) bis(1,2,3,4-tetrahydro-6,7,8-trimethoxy-2-methyl-1(3,4,5-trimethxoybenzyl)isoquinolinium) and a pharmaceutically acceptable anion.

4. The compound of claim 3 in which the compound is the racemic dl pair of the meso isomer.

5. The compound of claim 2 in which X is chlorine.

6. The compound of claim 2 in which the cation comprises approximately a 1:1 mixture of the racemic (dl) pair and the meso isomer.

7. The compound of claim 6 in which X is chlorine.

8. trans,trans-2,2'-(Dimethylenebis(carbonyloxytrimethylene)) bis(1,2,3,4-tetrahydro-6,7,8-trimethoxy-2-methyl-1-(3,4,5-trimethoxybenzyl)isoquinolinium)dichloride.

9. A pharmaceutical composition comprising the compound of claim 8 in a pharmaceutically acceptable carrier therefor.

10. A method of producing a long duration of muscle relaxation in a mammal which comprises parenterally adminstering an effective muscle relaxant amount of the compound of claim 3, to said mammal.

11. A method of producing a long duration of muscle relation in a mammal which comprises parenterally administering to said ammal an effective musCle relaxation amount of the compound or claim 7.

12. The method of producing muscle relaxation in a mammal which comprises parenterally administering an effective muscle relaxant amount of the compound of claim 8 to said mammal.

* * * * *

UNITED STATES PATENT AND TRADEMARK OFFICE

CERTIFICATE EXTENDING PATENT TERM
UNDER 35 U.S.C. 156

Patent No.    : 4,701,460

Dated         : October 20, 1987

Inventor(s)   : Hassan A. El-Sayad et al

Patent Owner  : Burroughs Wellcome Co.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

137 DAYS with all rights pertaining thereto as provided by 35 USC 156 (b).

I have caused the seal of the Patent and Trademark Office to be affixed this 24th day of April 1992.

Harry F. Manbeck, Jr.
Assistant Secretary and Commissioner
of Patents and Trademarks

UNITED STATES PATENT AND TRADEMARK OFFICE
CERTIFICATE OF CORRECTION

PATENT NO. : 4,701,460

DATED : October 20, 1987

INVENTOR(S) : El-Sayad, Hassan A.; Swaringen, Roy A.; and Yeowell, David A.

It is certified that error appears in the above-identified patent and that said Letters Patent is hereby corrected as shown below:

Column 5, lines 1-26
Claim 1, lines 2-27, the formula should appear as follows:

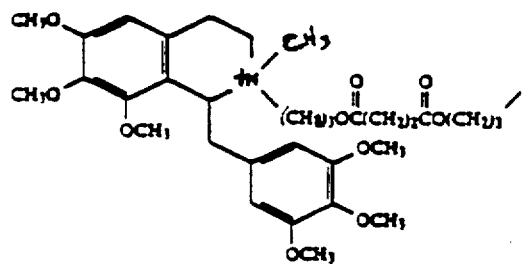

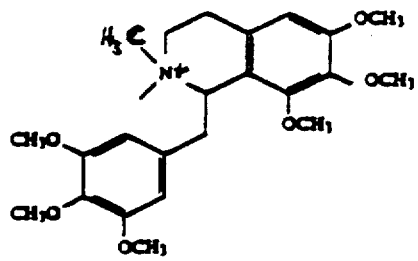

Column 5, line 30
Claim 2, line 2, delete "ad", and insert therefor --and--.

UNITED STATES PATENT AND TRADEMARK OFFICE
CERTIFICATE OF CORRECTION

PATENT NO. : 4,701,460

DATED : October 20, 1987

INVENTOR(S) : El-Sayad, Hassad A.; Swarigen, Roy A.; and Yeowell, David A.

It is certified that error appears in the above-identified patent and that said Letters Patent is hereby corrected as shown below:

Column 5, lines 32-45, and Column 6, lines 1-12
Claim 2, lines 5-24, the formula should appear as follows:

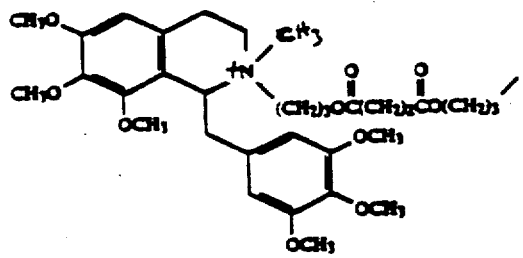

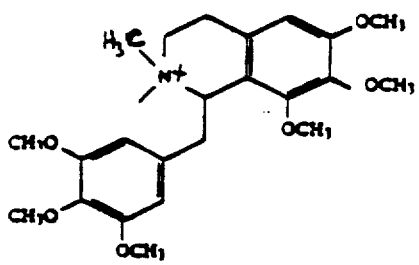

Column 6, line 13
Claim 2, last line, add the following: --wherein X is a pharmaceutically acceptable anion.--

UNITED STATES PATENT AND TRADEMARK OFFICE
CERTIFICATE OF CORRECTION

PATENT NO. : 4,701,460
DATED : October 20, 1987
INVENTOR(S) : El-Sayad, Hassan A.; Swaringen, Roy A.; and Yeowell, David A.

It is certified that error appears in the above-identified patent and that said Letters Patent is hereby corrected as shown below:

Column 6, lines 16-18
Claim 3, lines 2-4, after "cation" the compound name should read as follows: --trans,trans-2,2'-(dimethylenebis(carbonyloxytrimethylene))bis(1,2,3,4-tetrahydro-6,7,8-trimethyoxy-2-methyl-1-(3,4,5-trimethoxybenzyl)isoquinolinium)--.

Column 6, lines 27-30
Claim 8, the claim should read as follows:
--trans,trans-2,2'-(dimethylenebis(carbonyloxy-trimethylene))bis(1,2,3,4-tetrahydro-6,7,8-trimethoxy-2-methyl-1-(3,4,5-trimethoxybenzyl)isoquinolinium) dichloride--.

Column 6, lines 39 and 40
Claim 11, line 2, delete "relation", and insert therefor --relaxation--;
line 3, delete "ammal", and insert therefor --mammal--;
line 3, delete "musCle", as insert therefor --muscle--;

UNITED STATES PATENT AND TRADEMARK OFFICE
CERTIFICATE OF CORRECTION

PATENT NO. : 4,701,460

DATED : October 20, 1987

INVENTOR(S) : El-Sayad, Hassan A.; Swaringen, Roy A.; and Yeowell, David A.

It is certified that error appears in the above-identified patent and that said Letters Patent is hereby corrected as shown below:

Column 6, line 41
Claim 11, line 4, delete "or", insert therefor --of--.

Signed and Sealed this

Twenty-second Day of September, 1992

Attest:

DOUGLAS B. COMER

Attesting Officer

Acting Commissioner of Patents and Trademarks